United States Patent
Farmer et al.

(10) Patent No.: US 11,890,341 B2
(45) Date of Patent: *Feb. 6, 2024

(54) COMPOSITIONS AND METHODS FOR TREATING BIOFILM-RELATED LUNG CONDITIONS

(71) Applicant: Locus Solutions IPCo, LLC, Solon, OH (US)

(72) Inventors: Sean Farmer, North Miami Beach, FL (US); Ken Alibek, Solon, OH (US)

(73) Assignee: Locus Solutions IPCo, LLC, Solon, OH (US)

( * ) Notice: Subject to any disclaimer, the term of this patent is extended or adjusted under 35 U.S.C. 154(b) by 613 days.

This patent is subject to a terminal disclaimer.

(21) Appl. No.: 16/871,504

(22) Filed: May 11, 2020

(65) Prior Publication Data

US 2020/0353085 A1 Nov. 12, 2020

Related U.S. Application Data

(60) Provisional application No. 62/846,084, filed on May 10, 2019.

(51) Int. Cl.
| | | |
|---|---|---|
| *A61K 47/26* | (2006.01) | |
| *A61K 47/14* | (2017.01) | |
| *A61K 47/42* | (2017.01) | |
| *A61K 45/06* | (2006.01) | |

(52) U.S. Cl.
CPC ............. *A61K 47/26* (2013.01); *A61K 47/14* (2013.01); *A61K 47/42* (2013.01); *A61K 45/06* (2013.01)

(58) Field of Classification Search
CPC ........ A61K 47/26; A61K 47/14; A61K 47/42; A61K 45/06
See application file for complete search history.

(56) References Cited

U.S. PATENT DOCUMENTS

| | | |
|---|---|---|
| 4,902,512 A | 2/1990 | Ishigami et al. |
| 9,585,903 B2 | 3/2017 | Prabhune et al. |
| 2005/0031549 A1 | 2/2005 | Quay et al. |
| 2010/0074872 A1 | 3/2010 | Blaser et al. |
| 2012/0039853 A1 | 2/2012 | Corveleyn et al. |
| 2014/0255420 A1 | 9/2014 | Ilan et al. |
| 2015/0037302 A1 | 2/2015 | Bralkowski et al. |
| 2015/0094273 A1 | 4/2015 | Prabhune et al. |

FOREIGN PATENT DOCUMENTS

| | | |
|---|---|---|
| CN | 103007287 A | 4/2013 |
| CN | 103119158 A | 5/2013 |
| CN | 106456551 A | 2/2017 |
| CN | 107072944 A | 8/2017 |
| CN | 109689854 A | 4/2019 |
| EP | 0540074 A1 | 5/1993 |
| JP | 2003246717 A | 9/2003 |
| JP | 2014034552 A | 2/2014 |
| WO | WO 2015/153961 | * 10/2015 |
| WO | WO2015156904 | * 10/2015 |
| WO | WO2016063265 | * 4/2016 |

OTHER PUBLICATIONS

Palmeira de Oliveira et al. WO 2016063265, published: Apr. 28, 2016, English machine translation obtained on Nov. 5, 2022. (Year: 2022).*
Boisvert, A.-A., et al., "Microbial Biofilms in Pulmonary and Critical Care Diseases." Annals of the American Thoracic Society, 2016, 13(9): 1615-1623.
Elshikh, M., et al., "Rhamnolipids and lactonic sophorolipids: natural antimicrobial surfactants for oral hygiene." Journal of Applied Microbiology, 2017, 123: 1111-1123.
Joshi-Navare, K., et al., "A Biosurfactant-Sohporolipid Acts in Synergy with Antibiotics to Enhance Their Efficiency." BioMed Research International, 2013, vol. 2013, Article ID 512495, pp. 1-8.
De Brito, D., Biosurfactants from renewable raw materials, Universidade do Minho Departamento de Engenharia Biologica, Nov. 2013, pp. 1-93.
De Oliveira, M., et al., "Review: Sophorolipids a Promising Biosurfactant and it's Applications." International Journal of Advanced Biotechnology and Research, 2015, 6(2): 161-174.
Gharaei-Fathabad, E., "Biosurfactants in Pharmaceutical Industry (A Mini-Review)." American Journal of Drug Discovery and Development, 2010, 1(1): 58-69.
Kurtzman, C.P., et al., "Production of sophorolipid biosurfactants by multiple species of the *Starmerella* (Candida) bombicolayeast clade." FEMS Microbiol Lett, 2010, 311: 140-146.
Morikawa, M., "Beneficial Biofilm Formation by Industrial Bacteria Bacillus subtilis and Related Species." Journal of Bioscience and Bioengineering, 2006, 101(1): 1-8.
Nitschke, M., et al., "Production and properties of a surfactant obtained from Bacillus subtilis grown on cassava wastewater." Bioresource Technology, 2006, 97: 336-341.
Sen, R., "Biosurfactants: Advances in Experimental Medicine and Biology." Landes Bioscience and Springer Science+Business Media, LLC, 2010, 672: 1-331.
Sharma, A. et al., "A study on biosurfactant production in Lactobacillus and *Bacillus* sp." Int. J. Curr. Microbiol. App. Sci., 2014, 3(11): 723-733.
Sil, J., et al., "Health Care Applications of Different Biosurfactants: Review." International Journal of Science and Research (IJSR), 2015, 6(10): 41-50.

* cited by examiner

*Primary Examiner* — Genevieve S Alley
(74) *Attorney, Agent, or Firm* — SALIWANCHIK, LLOYD & EISENSCHENK

(57) ABSTRACT

The subject invention provides materials and methods for preventing, inhibiting or reducing biofilm formation and biofilm infections, in particular, in the respiratory tract of a subject. The invention utilizes growth by-products of beneficial microorganisms to enhance the effectiveness of biocidal substances in the treatment, disruption and/or prevention of biofilms. Advantageously, the subject invention is useful against antibiotic-resistant bacterial strains, such as MRSA, *Helicobacter pylori*, *S. pneumoniae*, *P. aeruginosa* and *A. fumigatus*.

8 Claims, No Drawings

COMPOSITIONS AND METHODS FOR TREATING BIOFILM-RELATED LUNG CONDITIONS

CROSS-REFERENCE TO RELATED APPLICATION

This application claims priority to U.S. Provisional Patent Application No. 62/846,084, filed May 10, 2019, which is incorporated herein by reference in its entirety.

BACKGROUND OF THE INVENTION

Antibiotics, which are the main tools in treating infections, are typically based on the efficiency of microbial killing studied in free-floating (planktonic) state, functioning as a single cell. Quantification of antibiotic efficacy is done in, for example, traditional Minimum Inhibitory Concentration (MIC) assays. However, certain microbial growth, including many human (and other animal) infections, are now understood to be caused, or exacerbated, by entire microbial colonies, often composed of microbes working together in a biofilm state. The biofilm comprises an adhesive extracellular component, which surrounds and protects the colony from environmental insult by, for example, antibiotics and the immune system.

Biofilms have broad-ranging clinical relevance in many areas of medicine. Bacterial biofilms such as those commonly associated with *Pseudomonas* and *Staphylococcus* are known to be a cause of intractable infection as well as chronic low-grade inflammation. The bacterial colonies in bacterial biofilms appear to be very resistant to the hosts' natural defenses as well as antibiotic treatments. Biofilms colonize virtually any surface to which these colonies can adhere. This includes surfaces in or on the human body. They often colonize biomaterials such as urinary catheters, transcutaneous intravenous lines and prosthetic heart valves.

Biofilms are initiated when free-floating, planktonic bacteria anchor to surfaces, such as, indwelling medical devices. The attached bacteria multiply and progress to form a microcolony, followed by a critical mass wherein bacterial crosstalk occurs, triggering a phenomenon known as quorum sensing. Quorum sensing leads to the biofilm phenotype, turning on biofilm-producing genes not expressed or produced in non-sessile bacteria. The bacteria respond collectively to express factors that are specific to the biofilm phenotype, which lead to the secretion of an exopolysaccharide (EPS) matrix surrounding and connecting the individual cells. The biofilm phenotype is characterized morphologically by the formation of microbial towers, which are composed of layers of embedded, live bacteria with intervening water channels. Under certain environmental conditions, the biofilm will release free-floating bacteria to disperse and continue the cycle at other locations and on other surfaces.

Biofilms behave differently from the same bacteria in free-floating form. Due to different genomic expression, biofilm-related infections have a different clinical course and antibiotic response than planktonic-type infections. Moreover, treating biofilm-associated infections as if they are planktonic infections leads to antibiotic-resistant bacteria. This is because the EPS matrix generated by the colony gives the colony the ability to develop resistance against antibiotics that would ordinarily kill the microbes in planktonic form.

When biofilms are present in the human body, the bacteria are far less susceptible to antibiotics, making certain infections, such as pneumonia, difficult to treat—and potentially lethal. Furthermore, because antibiotics fail to eradicate these EPS-protected microbial communities, use of antibiotics can compound the problem because antibiotics select for, and perpetuate, increasingly antibiotic-resistant bacteria. These bacteria include methicillin-resistant *Staphylococcus aureus* (MRSA), the world's leading cause of nosocomial infection, and a bacterium now widespread in the community at large.

Another pathogen with strong biofilm-forming capability is *Pseudomonas aeruginosa*, which is a gram-negative bacterium that causes acute and chronic infections, especially, when the host's defense system is compromised. *P. aeruginosa* produces exopolysaccharides, for example, Pel and Psl, that provide structural stability of biofilm and adherence to surface and other cells. Diseases involving *P. aeruginosa* infection include cystic fibrosis (CF), ventilator-associated pneumonia (VAP), and chronic obstructive pulmonary disease (COPD). Many antibiotics have become ineffective for treating *P. aeruginosa*, in part, because of its ability to form biofilms.

Cystic fibrosis (CF) is an autosomal recessive genetic disease that critically affects the lungs, the pancreas, the liver, and the intestine. CF is linked to mutations in the cystic fibrosis transmembrane conductance regulator (CFTR) gene, which significantly affects the respiratory, digestive and genital systems. The most serious symptom of CF patient is difficulty breathing due to clogging of the airways by mucus build-up and inflammation. *Staphylococcus aureus*, *Haemophilus influenzae*, and *P. aeruginosa* are the three most common organisms causing lung infections in CF patients.

Chronic obstructive pulmonary disease (COPD) is a disease characterized by persistently poor airflow due to the breakdown of lung tissue and dysfunction of the small airways. The common symptoms of COPD are sputum production, shortness of breath, and productive cough. Airway inflammation is also implicated in the development of COPD. The inflammation leads to protease-antiprotease imbalance, oxidant-antioxidant imbalance, which, in turn, causes alveolar destruction and bronchial mucous gland hypertrophy.

Fungal biofilms also play an important role in a range of pulmonary diseases. For example, the fungi *Aspergillus fumigatus* can cause chronic pulmonary aspergillosis (CPA) and Aspergilloma. The exopolysaccharides produced from *A. fumigatus* biofilm include galactomannan, galactosaminogalactan (GAG) and α-1, 3-glucan, which mediate adhesive ability of biofilm and maintain the integrity of the matrix.

Once organisms such as *P. aerugionosa* and *A. fumigatus* form biofilm in the respiratory tract, successful eradication is impossible because of the lung environment and bacterial resistance mechanisms. As a result, such infections eventually become chronic and the resulting persistent inflammation leads to reduced lung function.

Currently, antibiotics repeatedly fail to treat biofilm-associated infection. Moreover, there are no well-known or proven anti-biofilm treatments per se. In fact, not only are bacteria in biofilm state robustly resistant to antibiotics, they are also resistant to other anti-bacterials and biocides, such as alcohols, acids and iodine solutions.

Attempts to treat pathogenic biofilm infections include repeated and prolonged antibiotic therapy, physical removal of the biofilm (e.g., via surgery or debridement) and topical sterilizers, such as alcohol-based foams or gels. Unfortunately, however, these treatments fail to restore normal physiology, and disrupt the homeostasis of innate immunity. Antibiotics breed increasingly resistant bacteria; surgery or debridement results in anatomic wounding that creates another potential site for infection; and topical disinfectants may encourage development and growth of pathogenic biofilms by eradicating commensal microorganisms.

Biofilms can be the cause of a range of difficult-to-treat diseases and health conditions. Therefore, materials and methods are needed for treating and/or preventing biofilm formation, particularly with regard to biofilm infections in the respiratory tract of a subject.

BRIEF SUMMARY OF THE INVENTION

The present invention provides compositions and methods for treating, disrupting and/or preventing biofilm formation in the respiratory tract, in particular, in the lungs, as well as for treating and/or preventing the development of symptoms, comorbidities, and diseases associated with biofilm-associated infections in subjects. Advantageously, in certain embodiments, the present invention enhances current approaches for combatting antibiotic resistant strains of pathogenic bacteria.

The present invention also provides methods for preventing and/or treating biofilm-related infections in the respiratory tract of a subject. Specifically, the present invention provides methods for treating and/or preventing biofilm-associated infections in the lungs of a subject in need of such treatment and/or prevention. In some embodiments, the infection may be caused by *Staphylococcus, Haemophilus, Pseudomonas, Burkholderia, Aspergillus, Scedosporium, Candida, Exophiala, Penicillium* or *Acrophialophora.*

In further embodiments, the infection maybe caused by *Staphylococcus aureus, Haemophilus influenzae, Pseudomonas aeruginosa, Burkholderia cepacia, Aspergillus fumigatus, Aspergillus flavus, Aspergillus nidulans, Aspergillus terreus, Scedosporium apiospermum, Scedosporium prolificans, Candida albicans, Exophiala dermatitidis, Penicillium emersonii,* or *Acrophialophora fusispora.*

In certain embodiments, the methods of the present invention utilize a composition comprising one or more biological amphiphilic molecules (BAM) produced by, for example, a microorganism. Preferably, the composition further comprises one or more additional biocidal substances. Advantageously, the anti-biofilm composition is useful for eliminating biofilm having, or associated with, drug resistance, including MRSA, *Streptococcus pneumoniae, A. fumigatus* and *P. aeruginosa.* Furthermore, microbes do not readily acquire resistance to the treatments of the subject invention.

In specific embodiments, the one or more biocidal substances are, for example, antibiotics, including, for example, penicillins, tetracyclines, cephalosporins, quinolones, lincomycins, macrolides, sulfonamides, glycopeptides, aminoglycosides, and carbapenems.

In some embodiments, the biocidal substances can include essential oils, botanicals, or other plant extracts with bactericidal and/or anti-bacterial effects. These can include oils/extracts of, for example, tea tree, grapefruit, lemon, oregano, cinnamon, eucalyptus, citronella, thyme, and/or lavender.

In a preferred embodiment, the composition comprises one or more BAM, wherein the BAM are biosurfactants selected from, for example, glycolipids (e.g., sophorolipids, rhamnolipids, mannosylerythritol lipids, cellobiose lipids, and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes.

The one or more biosurfactants can further include any one or a combination of: a modified form, derivative, fraction, isoform, isomer or subtype of a biosurfactant, including forms that are biologically or synthetically modified.

In one embodiment, the one or more biosurfactants are present in the composition in critical micelle concentration (CMC). In certain embodiments, the one or more biosurfactants are isolated and/or purified.

The composition may have other components including, for example, carriers, pH modifiers, buffers, local anesthetic agents, agents that promote wound healing, agents that help degrade biofilm, agents that stop bleeding and/or promote clot formation, and other therapeutic and non-therapeutic components.

In certain embodiments, the composition attacks, dissolves or otherwise weakens the bacterial biofilm matrix, allowing for penetration of the biocidal substance to the individual cells of the biofilm-forming bacteria or fungi.

In preferred embodiments, the subject invention provides methods for treating, disrupting and/or preventing biofilm formation by administering the composition, either directly or indirectly, to the site of the biofilm, or to a site of potential biofilm formation.

In certain embodiments, the method is used to treat a subject who has been diagnosed as having a biofilm infection and/or who has been diagnosed as being at risk for acquiring a biofilm infection, wherein the method comprises: administering an effective amount of a composition comprising one or more microbial BAM, to a site in the patient having a biofilm, or potential for biofilm formation, thereon. In preferred embodiments, the composition further comprises one or more biocidal substances.

In one embodiment, the subject invention provides methods for prevention and/or treatment of diseases caused by, or associated with, biofilms or antibiotic resistant microbes.

In one embodiment, the composition can be administered to a site in a subject via localized delivery systems (e.g., a skin ointment, nasal spray, suppository, oral inhaler or nebulizer, ocular drop, pill or capsule, or oral liquid), directly to tissue that is affected by a biofilm or at risk of becoming affected.

DETAILED DESCRIPTION OF THE INVENTION

The present invention provides compositions and methods for treating, disrupting and/or preventing biofilm formation. This includes treating, disrupting and/or preventing biofilm formation in the respiratory system of a subject, as well as for treating and/or preventing the development of symptoms, comorbidities, and diseases associated with biofilm-associated infections in subjects. Specifically, the present invention provides compositions and method for treating and/or preventing biofilm-associated infections in the lungs. Advantageously, the present invention enhances current approaches for combatting antibiotic resistant strains of pathogenic bacteria.

Selected Definitions

As used herein, the term "subject" refers to an animal, such as a mammal, who has been infected by a biofilm-forming pathogen, or who is at risk of being infected therewith. The animal may be for example, pigs, horses, goats, cats, mice, rats, dogs, primates, e.g., apes, chimpanzees and orangutans, guinea pigs, hamsters, cows, sheep, birds, e.g., chickens, reptiles, fish, as well as any other vertebrate or invertebrate. The preferred subject in the context of this invention is a human of any gender. The subject can be of any age or stage of development, including infant, toddler, adolescent, teenager, adult, middle-aged and senior.

As subject who is "at risk" for a biofilm-related lung condition is one who, for example, has a genetic or pre-existing respiratory condition, such as a condition requiring oxygen supplementation, ventilation or intubation; has a history of smoking or chemical inhalation; is immunocompromised due to age or, for example, cancer; and/or lives in an area of the world where certain viral, bacterial or fungal contagions affecting the respiratory system are common.

As used herein, "infection" refers to the introduction and/or presence of a disease-causing, or pathogenic, organism into and/or in another organism, tissue or cell.

As used herein, a "biofilm" is a complex aggregate of microorganisms, such as bacteria or fungi, wherein the cells adhere to each other and/or to a surface. The cells in biofilms are physiologically distinct from planktonic cells of the same organism, which are single cells that can float or swim in liquid medium.

As used herein "preventing" or "prevention" of a disease, condition or disorder means delaying, inhibiting, suppressing, forestalling, and/or minimizing the onset or progression of a particular sign or symptom thereof. Prevention can include, but does not require, indefinite, absolute or complete prevention throughout a subject's lifetime, meaning the sign or symptom may still develop at a later time. Prevention can include reducing the severity of the onset of such a disease, condition or disorder, and/or inhibiting the progression of the condition or disorder to a more severe condition or disorder.

As used herein, "treating" or "treatment" of a disease, condition or disorder means the eradicating, improving, reducing, ameliorating or reversing of at least one sign or symptom of the disease, condition or disorder (e.g., an infection). Treatment can include, but does not require, a complete cure of the disease, condition or disorder, meaning treatment can also include partial eradication, improvement, reduction, amelioration or reversal.

As used herein, "respiratory tract" means a system of cells and organs functioning in respiration, in particular the organs, tissues and cells of the respiratory tract include, lungs, nose, nasal passage, paranasal sinuses, nasopharynx, larynx, trachea, bronchi, bronchioles, respiratory bronchioles, alveolar ducts, alveolar sacs, alveoli, pneumocytes (type 1 and type 2), ciliated mucosal epithelium, mucosal epithelium, squamous epithelial cells, mast cells, goblet cells, and intraepithelial dendritic cells.

As used herein, "control" in the context of a microorganism refers to killing and/or eradicating a microorganism, or otherwise reducing the population numbers and/or inhibiting pathogenicity or further growth of the microorganism at a particular site. In one embodiment, when a microorganism and/or a biofilm has caused an infection, controlling the microorganism and/or biofilm can be a form of treatment.

The terms "effective amount," and "effective dose" are used in this disclosure to refer to an amount of a compound or composition that, when administered to a site, is capable of providing a desired effect (e.g., control of a microorganism or treatment of an infection) at the site. The actual amount of the compound or composition will vary depending on a number of factors including, but not limited to, the particular microorganism being treated, the number of microorganisms present at the site, and in the case of a subject being treated for, e.g., a biofilm infection, the severity of the infection, the size and health of the subject, and the route of administering the compound or composition.

A plant "extract," as used herein, refers to the material resulting from exposing a plant part to a solvent and removing the solvent, or from using various chemical, immunological, biochemical or physical procedures known to those of skill in the art, including but not limited to, precipitation, steam distillation, centrifugation, filtering, column chromatography, detergent lysis and cold pressing (or expression). Plant extracts can include, for example, essential oils. Plant material can include roots, stems, leaves, flowers, or parts thereof.

The terms "isolated" or "purified," when used in connection with biological or natural materials such as nucleic acid molecules, polynucleotides, polypeptides, proteins, organic compounds, such as small molecules, microorganism cells/strains, or host cells, means the material is substantially free of other compounds, such as cellular material, with which it is associated in nature. That is, the materials do not occur naturally without these other compounds and/or have different or distinctive characteristics compared with those found in the native material.

In certain embodiments, purified compounds are at least 60% by weight the compound of interest. Preferably, the preparation is at least 75%, more preferably at least 90%, and most preferably at least 99% or 100% (w/w) of the desired compound by weight. Purity is measured by any appropriate standard method, for example, by column chromatography, thin layer chromatography, or high-performance liquid chromatography (HPLC) analysis.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially of" the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. All references cited herein are hereby incorporated by reference in their entirety.

Therapeutic Composition

In certain embodiments, the present invention utilizes a composition comprising one or more biological amphiphilic molecules (BAM) produced by, for example, a microorganism, and, preferably, one or more biocidal substances. Advantageously, in some embodiments, the anti-biofilm composition is useful for eliminating biofilm having, or associated with, drug resistance, including those formed by *S. pneumoniae*, *P. aeruginosa* and *A. fumigatus*. Furthermore, microbes do not readily acquire resistance to the treatments of the subject invention.

In one embodiment, the one or more BAM and one or more biocidal substances may promote the functions of each other in disrupting and treating biofilms. Accordingly, the combination of the one or more BAM and one or more biocidal substances exhibits advantageous properties in disrupting and treating biofilms, for example, when compared to any BAM or biocidal substances alone.

In a preferred embodiment, the administration of the disinfectant composition of the present invention to a site results in a reduction in the number of microorganisms and/or the formation of biofilm at the site when compared to an untreated site. Advantageously, in preferred embodiments, when administered to a site in a subject, the disinfectant composition according to the present invention can result in effective control and/or prevention of a biofilm-related infection without causing tissue damage.

Advantageously, in preferred embodiments, ingredients of the composition of the current invention work together to disrupt and/or inhibit biofilm formation and biofilm-associated infections while improving associated chronic inflammatory conditions through enhancement of pathogenic biofilm dispersion as well as improvement of the normal, local innate immune response.

In specific embodiments, the one or more biocidal substances are, for example, antibiotics, including, for example, penicillins (such as penicillin G, penicillin V, ampicillin, amoxicillin, bacampicillin, carbenicillin, carbenicillin indanyl, ticarcillin, azlocillin, mezlocillin, methicillin, piperacillin, and the like), tetracyclines (such as chlortetracycline, oxytetracycline, methacycline, doxycycline, minocycline and the like), cephalosporins (such as cefadroxil, cephalexin, cephradine, cephalothin, cephapirin, cefazolin, cefaclor, cefamandole, cefonicid, cefoxitin, cefotetan, cefuroxime, cefuroxime axetil, cefinetazole, cefprozil, loracarbef, ceforanide, cefepime, cefoperazone, cefotaxime, ceftizoxime, ceftriaxone, ceftazidime, cefixime, cefpodoxime, ceftibuten, and the like), fluoroquinolones (e.g., levofloxacin), quinolones (such as nalidixic acid, cinoxacin, ciprofloxacin and norfloxacin and the like), lincomycins (e.g., clindamycin), macrolides (e.g., erythromycin, azithromycin), sulfones (e.g., dapsone), sulfonamides (e.g., sulfanilamide, sulfadiazine, sulfamethoxazole, sulfisoxazole, sulfacetamide, bactrim), lipopeptides (e.g., daptomycin), polypeptides (e.g., bacitracin), glycopeptides (e.g., vancomycin), aminoglycosides (e.g., streptomycin, gentamicin, tobramycin, amikacin, netilmicin, kanamycin, and the like), nitoimidazoles (e.g., metronidazole) and/or carbapenems (e.g., thienamycin).

Certain specific examples of antibiotics or anti-infectives according to the subject invention include, but are not limited to, ampicillin, doxycycline, cephalexin, ciprofloxacin, sulfacetamide, clindamycin, metronidazole, erythromycin, azithromycin, sulfamethoxazole, amoxicillin, oxytetracycline, tetracycline, streptomycin, dapsone, methicillin, penicillin, vancomycin, bacitracin, daptomycin, bactrim, tobramycin, p-aminobenzoic acid, diaminopyrimidine, β-lactam, β-lactamase inhibitor, glycopeptide, chloraphenicol, macrolide, corticosteroid, prostaglandin, ciprofloxacin, linomycin, clindamycin, spectinomycin, polymyxin B, colistin, isoniazid, rifampin, ethambutol, ethionamide, aminosalicylic acid, cycloserine, capreomycin, sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, terbinafine, levofloxacin and any combination thereof.

In some embodiments, the biocidal substances can include essential oils, botanicals, or other plant extracts with bactericidal and/or anti-bacterial effects. These can include oils/extracts at a concentration between 1-10% volume/volume (extract/invention), horseheal (*Inula helenium, L. Asteraceae*, elecampane), rose (*Rosa damascena L., Rosaceae*), lavender (*Lavandula angustifolia L., Labiatae*), chamomile (*Matricaria recutica L., Asteraceae*), orange (*Rutaceae*), grapefruit (*Citrus paradisi*), eucalyptus (*Eucalyptus globulus L., Myrtaceae*), geranium (*Geranium robertianum L., Geraniaceae*), juniper (*Juniperus communis L., Cupressaceae*), citrus (*Citrus sinensis L., Rutaceae*), tea tree (*Melaceuca alternifolia*), manuka bush (*Leptospermum scoparium*), neem tree (*Azadirachta indica, A. Juss*), tea plant (*Camellia sinensis*), rosemary (*Rosmarinus officinalis L., Lamiaceae*), lemon, oregano, cinnamon, eucalyptus, citronella, and thyme oils.

Other known biocides, including non-therapeutic biocides, can also be utilized, such as alcohols, aldehydes, chlorine, and chlorine-releasing agents (e.g., sodium hypochlorite, chlorhexidine, chlorhexidine gluconate), iodine, peroxygen compounds (e.g., hydrogen peroxide, peracetic acid), phenolic type compounds, quaternary ammonium compounds (e.g., benzalkonium chloride), bases (e.g., sodium hydroxide, potassium hydroxide, sodium carbonate), and acids (e.g., mineral and organic acids).

In a preferred embodiment, the composition further comprises one or more BAM, wherein the BAM are biosurfactants selected from, for example, low molecular weight glycolipids (e.g., sophorolipids, rhamnolipids, mannosylerythritol lipids, cellobiose lipids, and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes.

The one or more biosurfactants can further include any one or a combination of: a modified form, derivative, fraction, isoform, isomer or subtype of a biosurfactant, including forms that are biologically or synthetically modified.

In one embodiment, the one or more biosurfactants are present in the composition in critical micelle concentration (CMC). In certain embodiments, the one or more biosurfactants are isolated and/or purified.

In certain embodiments, the concentration of BAM is about 5% or less, preferably about 0.5% to about 2.5%, more preferably about 0.7 to 1.5%.

In a specific embodiment, the BAM is a surfactant, preferably a biosurfactant. Biosurfactants are surface active compounds that lower the surface and interfacial tension between individual molecules at respective surfaces and interfaces. Among other capabilities, biosurfactants provide additional immune support against viral infections, and enhance the bioavailability of the other active components.

Biosurfactants are biodegradable and can be produced using selected organisms on renewable substrates. Most biosurfactant-producing organisms produce biosurfactants in response to the presence of a hydrocarbon source (e.g., oils, sugar, glycerol, etc.) in the growing media. Other media components such as concentration of iron can also affect biosurfactant production significantly.

Microbial biosurfactants are produced by a variety of microorganisms, such as, for example, Pseudomonas spp. (*P. aeruginosa, P. putida, P. florescens, P. fragi, P. syringae*); *Flavobacterium* spp.; *Bacillus* spp. (*B. subtilis, B. pumillus, B. licheniformis, B. amyloliquefaciens, B. cereus*); *Wickerhamomyces* spp. (e.g., *W. anomalus*), *Candida* spp. (e.g., *C. albicans, C. rugosa, C. tropicalis, C. lipolytica, C. torulopsis*); *Rhodococcus* spp.; *Arthrobacter* spp.; *Campylobacter* spp.; *Cornybacterium* spp.; *Pichia* spp. (e.g., *P. anomala, P. guilliermondii, P. occidentalis*); *Starmerella* spp. (e.g., *S. bombicola*); and so on.

All biosurfactants are amphiphiles. They consist of two parts: a polar (hydrophilic) moiety and non-polar (hydrophobic) group. The hydrocarbon chain of a fatty acid acts as the common lipophilic moiety of a biosurfactant molecule, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

Due to their amphiphilic structure, biosurfactants increase the surface area of hydrophobic water-insoluble substances, increase the water bioavailability of such substances, and change the properties of bacterial cell surfaces. Biosurfactants accumulate at interfaces, thus reducing interfacial tension and leading to the foiiiiation of aggregated micellar structures in solution. The amphiphilic structure of biosurfactants allows for self-association and to interaction with biological membranes. The ability of biosurfactants to form pores and destabilize biological membranes permits their use as antibacterial, antifungal, and hemolytic agents. Combined with the characteristics of low toxicity and biodegradability, biosurfactants are advantageous for use in a variety of application, including human health.

In one embodiment, the biosurfactants according to the present invention are glycolipids, such as, for example, rhamnolipids, rhamnose-d-phospholipids, trehalose lipids, trehalose dimycolates, trehalose monomycolates, mannosylerythritol lipids, cellobiose lipids, ustilagic acid and/or sophorolipids (including lactonic and/or acidic forms).

In one embodiment, the biosurfactants can comprise one or more lipopeptides, such as, for example, surfactin, iturin, fengycin, arthrofactin, viscosin, amphisin, syringomycin, and/or lichenysin.

In one embodiment, the biosurfactants can comprise one or more other types of biosurfactants, such as, for example, cardiolipin, emulsan, lipomanan, alasan, and/or liposan.

In preferred embodiments, the composition comprises a glycolipid biosurfactant. In a specific embodiment, the glycolipid is a purified SLP. SLP can be obtained from yeasts, such as *Starmerella bombicola* and *Wickerhamomyces anomalus*. SLP have antibacterial activity against, for example, *Escherichia coli, Moraxella* sp., *Ralstonia eutropha, Rhodococcus erythropolis*, and *Salmonella choleraesuis*. Additionally, SLP can inhibit microbial quorum sensing and destroy biofilms and/or inhibit their formation. This is particularly useful for treating infections, as biofilm formation by viruses and bacteria allows them to develop resistance to drugs and enhances their pathogenicity.

In some embodiments, the composition comprises a lipopeptide biosurfactant. In a specific embodiment, the lipopeptide biosurfactant is surfactin. Lipopeptides are produced by a variety of probiotics and non-pathogenic bacteria, such as, e.g., *Bacillus natto, Bacillus coagulans, Bacillus subtilis, Bacillus amyloliquefaciens*, lactic acid bacteria, and others.

Surfactin, in particular, is one of the most powerful lipopeptide biosurfactants. Surfactin is produced by various *Bacillus subtilis* strains, and is indicated as having antimicrobial, antitumor, antiviral and antiadhesive properties. It can inhibit fibrin clot formation, induce formation of ion channels in lipid bilayer membranes, and inhibit cyclic adenosine monophosphate (cAMP).

In one embodiment, the surfactants can comprise one or more microbial-produced fatty acid ester compounds and/or fatty acid ether compounds having physical properties and/or behaviors similar to those of biosurfactants, but which are not commonly known as biosurfactants.

In certain embodiments, the fatty acid ester compounds can include, for example, highly esterified oleic fatty acids, such as oleic fatty acid ethyl esters and/or oleic fatty acid methyl esters (FAME).

In one embodiment, the BAM is a saponin. Saponins are surfactants that are found in many plants and that exhibit similar characteristics to microbial biosurfactants, for example, self-association and interaction with biological membranes. There are three basic categories of saponins, including triterpenoid saponins, steroidal saponins, and steroidal glycoalkaloids.

Some well-known triterpenoid saponin-accumulating plant families include the *Leguminosae, Amaranthaceae, Apiaceae, Caryophyllaceae, Aquifoliaceae, Araliaceae, Cucurbitaceae, Berberidaceae, Chenopodiaceae, Myrsinaceae* and *Zygophyllaceae*, among many others. Legumes such as soybeans, beans and peas are a rich source of triterpenoid saponins. The steroidal saponins are typically found in members of the Agavaceae, Alliaceae, Asparagaceae, Dioscoreaceae, Liliaceae, Amaryllidaceae, Bromeliaceae, Palmae and Scrophulariaceae families and accumulate in abundance in crop plants such as yam, alliums, asparagus, fenugreek, yucca and ginseng. The steroidal glycoalkaloids are commonly found in members of the Solanaceae family including tomato, potato, aubergines and capsicum.

One notable characteristic of many saponins and other biosurfactants is their ability to inhibit P-glycoproteins (P-gps). P-gp is a member of the ATP-dependent membrane transport proteins and is known to pump substrates out of cells in ATP-dependent mechanisms. The over-expression of P-gp in tumor cells reduces intracellular drug concentrations, which decreases the efficacy of a broad spectrum of antitumor drugs. Accordingly, inhibiting P-gp potentially enhances the cellular bioavailability of some of these compounds.

Thus, in some embodiments, biosurfactants, such as saponins, contribute to the effectiveness of the composition by, for example, enhancing the bioavailability of the other compounds present in the composition.

In certain embodiments, the composition attacks, dissolves or otherwise weakens the bacterial biofilm matrix, allowing for penetration of the biocidal substance to the individual cells of the biofilm-forming bacteria. The invention also allows antibiotics to be used at a lower amount, thereby decreasing toxicity and cost of treatment.

The composition may have other components including, for example, carriers, pH modifiers, buffers, local anesthetic agents, agents that promote wound healing, agents that help degrade biofilm, agents that stop bleeding and/or promote clot formation, and other therapeutic and non-therapeutic components, such as, for example, anti-viral agents, fungicidal agents, chemotherapeutic agents, topical antiseptics, anesthetic agents, oxygenated fluids and/or agents, diagnostic agents, homeopathic agents, and over-the-counter medications/agents.

In one embodiment, the composition may comprise one or more chelating agents, preferably selected from citric acid, phosphates, the di-, tri- and tetra-sodium salts of ethylene diamine tetraacetic acid (EDTA), the calcium salts of EDTA, ethylene glycol-bis-(b-aminoethylether)-N,N,N',N'-tetraacetic acid (EGTA); 1,2-bis(2-aminophenoxy)ethane-N,N,N',N'-tetraacetic acid (BAPTA); ethylene-N,N'diglycine (EDDA); 2,2'-(ethylendiimino)-dibutyric acid (EBDA); lauroyl EDTA; dilauroyl EDTA, triethylene tetramine dihydrochloride (TRIEN), diethylenetriamin-pentaacetic acid (DPTA), triethylenetetramine hexaacetic acid (TTG), deferoxamine (DFO), deferasirox (DSX), dimercaprol, zinc citrate, penicilamine, succimer, editronate, sodium hexmetaphosphate, edetate calcium disodium, D-penicillamine, polyphenols, gallol, catechol, dimercaprol, tetrathiomolybdate, lactoferrin, and clioquinol and combinations thereof.

Formulation and Delivery of the Composition

The compositions of the subject invention can be delivered to the affected tissues, e.g., lungs, by direct application, significantly increasing efficacy. In certain embodiments, the disinfectant composition can be formulated to be administered to a subject via any route of administration, including, for example, orally, via injection (e.g., intravenous (IV), intramuscular (IM), intraperitoneal, intrathecal or subcutaneous), transdermal, rectal, urogenital (e.g., vaginal), ocular, aural, nasal, inhalation and cutaneous routes.

The composition can be applied directly to an area affected by a biofilm, including surfaces such as human mucosa and keratinized and non-keratinized epithelium. Examples of such locally-directed therapies include skin medicaments, nasal sprays and washes, ear drops, rectal administration, oral inhalers and nebulizers, ocular drops, contact lenses, contact lens solutions, oral troches, dentifrices such as mouthwash, toothpaste, floss, and periodontal treatment. In each case, the composition of the present invention is administered via a vehicle whose composition is physiologically appropriate based on the site of administration.

In one embodiment, the components of the disinfectant composition are formulated as a mixture, comprising optional additional ingredients, such as, for example, one or more carriers (e.g., pharmaceutically-acceptable carriers) and/or excipients.

The tem "pharmaceutically acceptable" as used herein means compatible with the other ingredients of a pharmaceutical composition and not deleterious to the recipient thereof.

Carriers and/or excipients can be formulated into preparations in, for example, solid, semi-solid, liquid or gaseous forms, such as tablets, capsules, powders, granules, ointments, gels, lotions, solutions, suppositories, drops, patches, injections, inhalants and aerosols.

Carriers and/or excipients according the present invention can include any and all solvents, diluents, buffers (e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilisers (e.g., Tween 80, Polysorbate 80), colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatisers, thickeners, coatings, preservatives (e.g., Thimerosal, benzyl alcohol), antioxidants (e.g., ascorbic acid, sodium metabisulfite), tonicity controlling agents, absorption delaying agents, adjuvants, bulking agents (e.g., lactose, mannitol) and the like.

In some cases, the carriers can be, for example, sterile or non-sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration. The use of carriers and/or excipients in the field of drugs and supplements is well known. Except for any conventional media or agent that is incompatible with the supplement composition or with, its use in the present compositions may be contemplated.

In one embodiment, the supplement composition is formulated so that it can be delivered to a subject orally. In particular, the composition is formulated as an orally-consumable product.

Orally-consumable products according to the invention are any preparations or compositions suitable for consumption, for nutrition, for oral hygiene or for pleasure, and are products intended to be introduced into the human or animal oral cavity, to remain there for a certain period of time and then to either be swallowed (e.g., food ready for consumption) or to be removed from the oral cavity again (e.g. chewing gums or products of oral hygiene or medical mouth washes). These products include all substances or products intended to be ingested by humans or animals in a processed, semi-processed or unprocessed state. This also includes substances that are added to orally-consumable products (e.g., active ingredients such as extracts, nutrients, supplements, or pharmaceutical products) during their production, treatment or processing and intended to be introduced into the human or animal oral cavity.

Orally-consumable products can also include substances intended to be swallowed by humans or animals and then digested in an unmodified, prepared or processed state. These include casings, coatings or other encapsulations that are intended also to be swallowed together with the product or for which swallowing is to be anticipated.

The composition of the present invention can also be present in the form of capsules, tablets (uncoated and coated tablets, e.g., gastro-resistant coatings), coated tablets, granules, pellets, solid-substance mixtures, dispersions in liquid phases, as emulsions, powders, solutions, pastes or other swallowable or chewable preparations, or as a dietary supplement.

For oral administration, tablets or capsules can be prepared by conventional means with acceptable excipients such as binding agents, fillers, lubricants, disintegrants, or wetting agents. The tablets can be coated, if desired. Preparations for oral administration also can be suitably formulated to give controlled release of the active ingredients. Liquid preparations for oral administration can take the form of, for example, solutions, syrups, or suspensions, or they can be presented as a dry product for constitution with saline or other suitable liquid vehicle before use.

The formulation described herein can also contain acceptable additives as will be understood by one skilled in the art, depending on the particular fault of oral delivery. Non-limiting examples of such additives include suspending agents, emulsifying agents, non-aqueous vehicles, preservatives, buffer salts, flavoring, coloring, and sweetening agents as appropriate. Non-limiting examples of specific additives include: gelatin, glycerin, water, beeswax, lecithin, cocoa, caramel, titanium dioxide, and carmine.

In one embodiment, the composition can be formulated for administration via injection, for example, as a solution or suspension. The solution or suspension can comprise suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Other formulations can also include ocular drops, gel, ointment, cream or other vehicle of delivery of the composition appropriate to area of application, periocular lotion, intranasal aqueous or non-aqueous spray, nasal saline rinse, skin soap, lotion, cream, emollient, and solution such as meant for contact lens cleaning and maintenance or spray.

In one embodiment, the supplement composition is formulated into a self-forming delivery system, wherein a BAM forms a lipo some, or micro- or nanocapsule, with the biocidal component(s) encapsulated therein. In one embodiment, additional biological polymers can be included to provide further structure for encapsulation.

BAM encapsulation can enhance the bioavailability of the biocidal component(s) by protecting it from components in the blood, such as proteins and other molecules, that otherwise might bind to the compound and prevent it from penetrating a target site. Additionally, the encapsulated delivery system can allow for compounds that might otherwise be degraded by acids or enzymes in the GI tract to be administered orally, as it creates a barrier against the acids or enzymes. Furthermore, the BAM-encapsulated delivery system formulation allows for time release of the compound(s) therein, thereby reducing the potential toxicity or potential negative side-effects in a subject.

Further components can be added to the compositions as are determined by the skilled artisan such as, for example, buffers, carriers, viscosity modifiers, preservatives, flavorings, dyes and other ingredients specific for an intended use. One skilled in this art will recognize that the above description is illustrative rather than exhaustive. Indeed, many additional formulations techniques and pharmaceutically-acceptable excipients and carrier solutions suitable for particular modes of administration are well-known to those skilled in the art.

In one embodiment, the pH of the formulations is between about 5.5 and 8.0, between about 6.0 and 8.0, and about 6.5 and 8.0, more preferably between about 6.5 and 7.5, most preferably between about 7 and 7.4. The preferable pH assists in avoiding bacterial resistance to the formulations.

Methods

The present invention provides methods for preventing and/or treating biofilm-related infections in the respiratory tract of a subject. Specifically, the present invention provides methods for treating and/or preventing biofilm-associated infections in the lungs of a subject. In some embodiments, the infection may be caused by *E. coli, Staphylococcus, Stenotrophomonas, Haemophilus, Klebsiella* spp, *Pseudomonas, Burkholderia, Aspergillus, Scedosporium, Chlamydia, Candida, Exophiala, Penicillium* or *Acrophialophora*.

In further embodiments, the infection maybe caused by *Streptococcus pneumoniae Staphylococcus aureus, Stenotrophomonas maltophilia, Haemophilus influenzae, Pseudomonas aeruginosa, Mycoplasma pneumonia, Burkholderia cepacia, Aspergillus fumigatus, Aspergillus flavus, Aspergillus nidulans, Aspergillus terreus, Scedosporium apiospermum, Scedosporium prolificans, Candida albicans, Exophiala dermatitidis, Penicillium emersonii,* or *Acrophialophora fusispora*.

In preferred embodiments, the subject invention provides methods for treating, disrupting and/or preventing biofilm formation in the respiratory tract of a subject by administering a composition comprising one or more biological amphiphilic molecules. In preferred embodiments, the composition further comprises one or more biocidal compounds. In one embodiment, the methods can be used for prevention and/or treatment of diseases caused by, or associated with, biofilms or antibiotic resistant microbes.

In specific embodiments, the one or more biocidal substances are, for example, antibiotics, including those listed previously, for example, penicillins, tetracyclines, cephalosporins, quinolones, lincomycins, macrolides, sulfonamides, glycopeptides, aminoglycosides, and carbapenems.

In some embodiments, the biocidal substances can include essential oils, botanicals, or other plant extracts with bactericidal and/or anti-bacterial effects. In some embodiments, the biocidal substances can include therapeutic or non-therapeutic biocides, such as alcohols, chlorhexidine (e.g., CHG), or hydrogen peroxide.

In a preferred embodiment, the composition further comprises one or more BAM, wherein the BAM are biosurfactants selected from, for example, weight glycolipids (e.g., sophorolipids, rhamnolipids, mannosylerythritol lipids, cellobiose lipids, and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes. In one embodiment, the BAM is a saponin.

In certain embodiments, the site of application of the anti-biofilm composition has a biofilm thereon or is a potential site for biofilm formation. In one embodiment, subject invention is effective in dispersing and eliminating newly-formed biofilm as well as aged and/or chronic biofilms, such as those formed for at least 1 day, 2 days, 5 days, 1 week, 2 weeks, 3 weeks, or 1 month or more.

In certain embodiments, the disinfectant treatment is used to treat a subject who has been diagnosed as having a biofilm infection and/or who has been diagnosed as being at risk for acquiring a biofilm infection, wherein the method comprises: administering an effective amount of a composition comprising one or more biocidal substances and one or more microbial BAM, to a site in the patient.

The methods can be used to prevent and/or treat biofilm-related infections of a variety of sites in a subject's body. For example, the composition can be administered via localized delivery systems (e.g., a skin ointment, nasal spray, oral inhaler or nebulizer, ocular drop, or oral liquid), directly to tissue that is affected by a biofilm or at risk of becoming affected.

In one embodiment, the site can be any site in a subject's body that is at a risk of developing a biofilm-associated infection or has an existing infection that is associated with the formation of biofilm. In certain embodiments, the site is selected from the oral cavity, the nasal cavity, the respiratory tract, the digestive tract (including intestines, stomach, and colon), the urogenital tract, the eyes, the sinuses, surgical sites, implants and on the skin. In some embodiments, the composition is applied directly or indirectly to the site.

In specific embodiments, the site having a biofilm-associated infection or having a risk of developing a biofilm-associated infection is selected from lungs, nose, nasal passage, sinuses, trachea, bronchi, bronchioles, respiratory bronchioles, alveolar ducts and surgical sites.

In a specific embodiment, the patient is first diagnosed with a biofilm infection prior to treatment with a composition of the present invention. The subject may also be monitored after and/or during treatment to access the efficacy of the treatment.

The location of biofilm infections can be determined by imaging techniques such as, for example, X-ray and CT scans. In one embodiment, biofilm infection can be detected by obtaining a biological sample from a subject; and measuring the presence of one or more biomarkers (e.g., exopolysaccharide, proteins, mRNA) that are associated with and/or selectively expressed by microorganisms in a biofilm state, but not in a free-floating (planktonic) state.

In another embodiment, biofilm infection can be detected by the presence of bacterial extracellular polysaccharide (EPS) matrix, or chemicals contained in the EPS.

Further, species of drug resistant microbes and/or pathogenic microorganisms that form biofilm can be determined by, for example, using antibodies that recognize antigens or peptides associated with the presence of pathogenic microorganisms, or using probes that recognize nucleic acid molecules of the pathogenic microorganisms.

The term "biological sample," as used herein, includes but is not limited to, a sample containing tissues, cells, and/or biological fluids isolated from a subject. Examples of biological samples include but, are not limited to, tissues, cells, biopsies, blood, lymph, serum, plasma, urine, cerebrospinal fluid, saliva, and tears. In certain specific embodiments, the biological samples include blood, tears, nasal fluid, and saliva.

The presence and/or level of biomarkers useful according to the subject invention can be determined by techniques known in the art, such as for example, enzyme-linked immunosorbant assays (ELISA), Western blot, Northern Blot, immunological assays, immunofluorescence, and nucleic acid hybridization techniques.

In one embodiment, the biofilm infection has been determined to be resistant to an antibiotic. Advantageously, the anti-biofilm compositions of the subject invention are useful for eliminating biofilm or reducing the formation of biofilm, even in drug-resistance strains of bacteria. Furthermore, the subject invention is useful in reducing bacterial drug resistance.

In one embodiment, the anti-biofilm composition can be administered in conjunction with a chemotherapeutic agent and/or other cancer therapy.

Anti-biofilm efficacy of compositions, including the compositions of the present invention, may be assessed using the Calgary Biofilm Device, an FDA Class I approved device for the inoculation of biofilms (U.S. Pat. No. 6,599,714, herein incorporated by reference) to perform the MBEC (Minimum Biofilm Eradication Concentration) procedure or other means of assessing anti-biofilm efficacy. Other anti-microbial tests that can be employed include: the agar or disk-diffusion technique, the Kirby-Bauer test and the Minimum Inhibitory Concentration (MIC). These techniques are well known to those versed in the art and will not be recounted in detail here. Protocols may be found in "Techniques in Microbiology" by John Lammert, Pearson Education, 2007, and "Microbiology Laboratory Fundamentals and Applications" by George A. Wistreich, Pearson Education, 2003, which are incorporated by reference in their entirety.

Anti-biofilm efficacy (Biofilm Inhibitory Concentration or BIC) can be compared directly against planktonic efficacy by performing the Minimum Inhibitory Concentration (MIC) test for the same anti-microbial compounds and micro-organisms being tested. Additionally, antibiofilm efficacy can be measured using a classification system similar to the manuka factor (Molan, Peter, "Method for the assay of antibacterial activity of honey", 2005, herein incorporated by reference), except that, in this case, what is measured is the size of complete biofilm growth inhibition (biofilm inhibitory concentration, or BIC), rather than the killing diameter ("zone of inhibition") of antimicrobial substances of compounds such as honey. This procedure will be used to develop BIC standards of the compositions against a range of bacteria as well as bacterial groups such as gram negative bacteria, methicillin sensitive and methicillin resistant *Staphylococcus*, et cetera.

In embodiments of the present invention, administration of the anti-biofilm composition occurs daily for several days or longer. Administration can include any known method of drug administration, including, but not limited to, oral, nasal, cutaneous, intravenous administration, or otherwise as is described herein. In one embodiment, the supplement composition is applied to a site once, twice, or three times per day, determined on a subject-by-subject basis by a skilled physician. Factors to be considered when determining the number of doses to administer include the age of the individual receiving treatment and the severity of the subject's symptoms.

In one embodiment, the method further comprises performing follow-up tests on the subject to determine whether, and/or to what extent, the infection has been treated. The subject can be monitored throughout the course of treatment, for example, every day or every other day, in order to determine the status of the infection and whether or not the composition is effectively treating the infection. This can include, for example, performing tests, such as those used for diagnosing the infection, as well as observing the subject for signs of improving health. If follow-up tests show that the rate of improved health is below that which is desired, the dosage of the composition can be adjusted as determined by the skilled practitioner.

The anti-biofilm compositions of the subject invention can be delivered to a site by many routes, using a wide range of currently-available delivery devices, systems, and methods. These routes include, for example, cutaneous, intra-abdominal, intracranial, intralesional, intrathoracic (during surgery), nasal, in the ear canal, as an oral bowel prep, gastric lavage, as an eye wash, periodontal, rectal, soft tissue, subcutaneous, and vaginal routes.

Delivery can be performed via catheter to treat infection caused by a range of pathogenic biofilms, or potential pathogenic biofilms, including, but not limited to, respiratory tract infections, urinary tract infections, bloodstream infections, intracranial infections, and joint infections.

In one embodiment, the composition can be administered via inhalation, for example, to treat an infection in the respiratory tract, e.g., the lungs, of a subject. In one embodiment, the infection is caused by, causes, or is associated with the following lung conditions: cystic fibrosis (CF); asthma; chronic obstructive pulmonary disease (COPD); pulmonary hypertension; lung cancer; pulmonary fibrosis; bronchiectasis; acute respiratory distress syndrome; emphysema; pneumoconiosis; tuberculosis; nontuberculous mycobacterial (NTM) pulmonary infections; coronaviruses, such as SARS-CoV, MERS-CoV, and SARS-CoV-2; or pneumonia including, but not limited to, ventilator associated pneumonia, community acquired pneumonia, bronchial pneumonia, and lobar pneumonia.

In one embodiment, the subject may be intubated or ventilated patients, recipients of a lung transplant, patients having been diagnosed with CF, COPD, bronchitis (such as chronic bronchitis and acute bronchitis), pertussis (whooping cough), SARS, MERS, Covid-19, inner ear infections, streptococcal throat infections, inhalation anthrax, tularemia, pulmonary hypertension, lung cancer, pulmonary fibrosis, bronchiectasis, acute respiratory distress syndrome, emphysema, pneumoconiosiss, tuberculosis, nontuberculous mycobacterial (NTM) pulmonary infections, pneumonia or sinusitis. In one embodiment, the patient has CF or COPD. In one embodiment, the patient has allergic bronchopulmonary aspergillosis.

In specific embodiments, the composition is formulated for inhalation by CF or COPD patients who have developed a lung infection that associated with biofilm, or who are at risk for developing such an infection. In a specific embodiment, the subject has been diagnosed with CF or COPD.

In one embodiment, the composition is effective in reducing the inflammation caused by the infections. Reduction can be an at least 5%, 10%, 15%, 20%, 25%, 30%, 35%, 40%, 45%, 50%, 55%, 60%, 65%, 70%, 75%, 80%, 85%, 90%, 95%, 99%, or essentially complete reduction in inflammation or infection, or about any of the aforementioned numbers, or a range bounded by any two of the aforementioned numbers.

In one embodiment, the subject invention provides methods for preventing, reducing and treating an inflammation caused by a biofilm-associated infection in a subject, wherein said method comprises administering to the subject a composition comprising one or more biological amphiphilic molecules (BAM) and, optionally, one or more biocidal substances. Preferably, the inflammation is caused by respiratory tract infections, urinary tract infections, bloodstream infections, intracranial infections, and joint infections. More preferably, the inflammation is a lung infection caused by the formation of biofilm.

In one embodiment, the composition comprising BAM and/or antibiotics is administered into the subjection over a period so that treatment infection results in an increase in forced expiratory volume (FEV). Increase can be an at least 2%, 5%, 10%, 15%, 20%, 25%, 30%, 35%, 40%, 45%, 50%, 55%, 60%, or about any of the aforementioned numbers, or a range bounded by any two of the aforementioned numbers.

In one embodiment, the composition can be administered via a syringe to treat and/or prevent spinal cord infections including, but not limited to, for example, meningitis.

In one embodiment, the composition can be administered via a spray or mist to treat appropriate sites such as chronic wounds and burns, or for nasal administration or as a full-body or partial-body shower to disinfect a subject who has been, or is suspected of having been, exposed to a pathological agent such as, for example, in the context of a biological weapon.

In one embodiment, the composition can be administered to a site of healing tissue. For the purpose of this invention, a healing tissue site is an area of the tissue that suffered an injury or a disease and is recovering after the treatment for the injury or the disease. A healing tissue site can be at the surface of the respiratory tract or lungs.

In one embodiment, the composition can be administered via a tablet taken orally, microcapsule delivery spheres, nanoparticles, targeted nanoparticles (for example, receptor mediated targeted nanoparticles), a time controlled delivery system, a frozen block of the sterile disinfectant composition, a plain aqueous solution of the active agent, an isotonic solution of the active agent, or an implantable time release delivery system.

In certain embodiments, the composition is left at the site after administration thereto. In a further embodiment, the site or the tissue is rinsed with, for example, a sterile solution free of the active agent. Examples of solutions free of the active agent include, but are not limited to, plain water, saline, and isotonic solutions free of the active agent. The rinsing can be performed by administering the solution free of the active agent to the site and removing the resultant solution from the site or the tissue by, for example, suction. In certain embodiments, the rinsing is performed within about 1 minute to about 10 minutes, about 2 minutes to about 5 minutes, or about 3 minutes from the time of administering the composition to the site in the subject. In other embodiments, suction is performed, with or without rinsing.

Doses for use in the methods according to the subject invention may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history).

Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The composition for treating the biofilm-associated infection may comprise one or more antibiotic between about 0.01 mg/dose and 3000 mg/dose, between about 0.1 mg/dose and 2000 mg/dose, between about 1 mg/dose and 1500 mg/dose, between about 10 mg/dose and 1000 mg/dose, between about 20 mg/dose and 800 mg/dose, between about 50 mg/dose and 500 mg/dose, between about 100 mg/dose and 300 mg/dose, or between about 100 mg/dose and 200 mg/dose. Preferably, the antibiotic is provided in the inhalable composition at about 10 mg/dose, 20 mg/dose, 30 mg/dose, 50 mg/dose, 100 mg/dose, 150 mg/dose, 200 mg/dose, 250 mg/dose, 200 mg/dose or 300 mg/dose.

The total amount of antibiotic per day may be between about 0.01 mg/day and 6,000 mg/day, between about 0.1 mg/day and 5,500 mg/day, between about 1 mg/day and 5,000 mg/day, between about 10 mg/day and 4,500 mg/day, between about 20 mg/day and 4,000 mg/day, between about 30 mg/day and 3,000 mg/day, between about 50 mg/day and 2,000 mg/day, between about 100 mg/day and 2,000 mg/day, between about 150 mg/day and 2,000 mg/day, between about 200 mg/day and 2,000 mg/day, between about 250 mg/day and 2,000 mg/day, between about 300 mg/day and 1,500 mg/day, between about 500 mg/day and 1,000 mg/day, or between about 800 mg/day and 1,000 mg/day. Preferably, the antibiotic is provided in the inhalable composition at about 200 mg/day, 300 mg/day, 500 mg/day, 1,000 mg/day or 1,250 mg/day.

The composition for treating the biofilm-associated infection comprises one or more BAM between about 0.01 mg/dose and 3000 mg/dose, between about 0.1 mg/dose and 2000 mg/dose, between about 0.5 mg/dose and 1000 mg/dose, between about 1 mg/dose and 1000 mg/dose, between about 10 mg/dose and 1000 mg/dose, between about 20 mg/dose and 800 mg/dose, between about 50 mg/dose and 500 mg/dose, between about 100 mg/dose and 300 mg/dose, between about 100 mg/dose and 200 mg/dose, between about 0.1 mg/dose and 100 mg/dose, between about 0.5 mg/dose and 100 mg/dose, between about 1 mg/dose and 100 mg/dose, between about 5 mg/dose and 100 mg/dose, between about 10 mg/dose and 100 mg/dose or between about 0.1 mg/dose and 10 mg/dose. Preferably, the BAM is provided in the inhalable composition at about 0.1 mg/dose, 0.5 mg/dose, 1 mg/dose, 5 mg/dose, 10 mg/dose, 20 mg/dose, 30 mg/dose, 50 mg/dose, 100 mg/dose, 150 mg/dose, 200 mg/dose, 250 mg/dose, 200 mg/dose or 300 mg/dose.

Spectrum of Activity

The compositions and methods of the subject invention are suited for biofilms that grow aerobically and/or anaerobically. Control of biofilms can be achieved via a variety of mechanisms, including preventing, inhibiting, and/or disrupting the deposition, adhesion, and/or anchoring of biofilms or pathogenic microorganisms to biological or non-biological surfaces; preventing, inhibiting, and/or disrupting the secretion and/or release of extracellular factors such as exopolysaccharide (EPS) matrix; and/or preventing, inhibiting, and/or disrupting quorum-sensing mechanisms. These pathogens include aerobic and anaerobic Gram-positive and Gram-negative bacteria.

In addition to eliminating, preventing or inhibiting the formation of biofilm, the composition of the subject invention can also "depathogenize" certain biofilm-forming bacteria, making these bacteria less potent to cause infection. Advantageously, administration of the disinfectant composition according to the subject invention can result in effective control of a biofilm related infection without causing tissue damage.

The microorganisms can be selected from, but are not limited to, *Streptococcus* spp. (e.g., *S. agalactiae*, *S. pneumoniae*, *S. pyogenes*, *S. salivarius*, and *S. sanguis*); *Staphylococcus* spp. (e.g., *S. aureus*, *S. epidermidis*, *S. haemolyticus*, *S. hominis*, and *S. simulans*, as well as oxacillin-resistant (ORSA) and oxacillin-susceptible staphylococci (also known as methicillin-resistant [MRSA] or methicillin-susceptible staphylococci)); *Acinetobacter* spp. (e.g., *A. fumigatus*, *A. flavus*); *Acrophialophora* spp. (e.g., *A. fusispora*); *Aspergillus* spp. (e.g., *A. nidulans*, *A. terreus*); *Bacteroides* spp. (e.g., *B. fragilis*); *Burkholderia* spp. (e.g., *B. cepacia*); *Candida* spp. (e.g., *C. albicans*); *Chlamydia* spp.; *Clostridium difficile; Enterobacter* spp.; *Enterococcus* spp. (e.g., *E. faecalis* and *E. faecium*, vancomycin-susceptible and vancomycin-resistant strains); *Escherichia coli; Exophiala* spp. (e.g., *E. dermatitidis*); *Francisella* spp.; *Haemophilus* spp. (e.g., *H. influenzae*); *Helicobater* spp. (e.g., *H. bilis*, *H. bizzozeronii*, *H. canadensis*, *H. canis*, *H. cinaedi*, *H. fennelliae*, *H. heilmannii*, *H. hepaticus*, *H. pullorum*, *H. pylori*, *H. rappini*, *H. salmonis*, and *H. suis*); *Klebsiella* spp. (e.g., *K. aerogenes*, *K. pneumonia*); *Mycoplasma pneumonia; Penicillium emersonii; Propionibacterium* spp.; *Proteus mirabilis; Pseudomonas* spp. (e.g., *P. aeruginosa*); *Salmonella* spp.; *Scedosporium* spp. (e.g., *S. apiospermum*, *S. prolificans*); *Selenomonas* spp.; *Stenotrophomonas* spp. (e.g., *S. maltophilia*); *Veillonella* spp.; and *Yersinia pestis*.

Conditions Associated With Biofilm Infections

Advantageously, the present invention can lead to simultaneous improvement of diseases, disorders and conditions caused by biofilm infections, reduction in the occurrence of biofilm infections, and reduction in the development of antibiotic-resistant strains of the bacteria.

In certain embodiments, the subject invention can be used to prevent, treat, or ameliorate diseases caused by or associated with biofilm. These can include, but are not limited to, sepsis, septicemia, allergies, asthma, aspergillosis, "swimmer's ear," otitis externa, otitis media, chronic otitis, atopic dermatitis, chronic rhinosinusitis, chronic sinusitis, allergic rhinitis, allergic conjunctivitis, chronic bronchitis, cystic fibrosis, nasal infection, sinus infection, pink eye, eye infections, dry eye syndrome, migraines, anxiety, depression, chronic gingivitis, chronic periodontitis, stomach pain, nausea, vomiting, peptic ulcers, stomach cancer, gastritis, GI bleeding, diarrhea, constipation, gas, bloating, food sensitivities, heartburn, acid-reflux, GERD, indigestion, IBS, cancer (e.g., colon cancer), eczema dermatitis, acne, chronic non-healing wounds, chronic cystitis, bchronic blepharitis, meibomianitis, rosacea, atherosclerosis, coronary heart disease, acute ischemic stroke, myocardial infarction, hepatocellular carcinoma, cirrhosis and hepatic encephalopathy, nonalcoholic fatty liver disease and fibrosis, acute and chronic pancreatitis pathogenesis, autoimmune pancreatitis, diabetes mellitus and metabolic syndrome, chronic tonsillitis, and adenoiditis.

In certain embodiments, the subject invention can be used to prevent, treat, or ameliorate lung diseases caused by or associated with biofilm. These lung diseases may include, but not limited to, cystic fibrosis (CF); asthma; chronic obstructive pulmonary disease (COPD); pulmonary hypertension; lung cancer; pulmonary fibrosis; bronchiectasis; acute respiratory distress syndrome; emphysema; pneumoconiosis; tuberculosis; nontuberculous mycobacterial (NTM) pulmonary infections; SARS, MERS, Covid-19, or other coronaviruses; or pneumonia including, but not limited to, ventilator associated pneumonia, community acquired pneumonia, bronchial pneumonia, and lobar pneumonia.

In one embodiment, the invention is used to prevent or reduce the formation of biofilm in or on inanimate objects, for example, ventilators, endotracheal tubes, oxygen masks, surgical implants, stents, catheters, and other indwelling medical devices.

We claim:

1. A method for disrupting and treating a biofilm-associated infection in the lungs of a subject in need, wherein said method comprises administering to the subject a composition comprising two or more yeast growth by-products, said two or more yeast growth by-products comprising a sophorolipid (SLP) and a mannosylerythritol lipid (MEL); and a biocidal substance.

2. The method of claim 1, comprising a biocidal substance selected from penicillins, tetracyclines, cephalosporins, quinolones, lincomycins, macrolides, sulfonamides, glycopeptides, aminoglycosides, and carbapenems.

3. The method of claim 1, comprising a biocidal substance selected from cephalexin, cefadroxil, clindamycin, clarithromycin, azithromycin, cefdinir, cefpodoxime, amoxicillin, ampicillin, and penicillin.

4. The method of claim 1, comprising a biocidal substance selected from essential oils, botanicals and/or plant extracts with anti-bacterial effects.

5. The method of claim 1, wherein the subject is a human.

6. The method of claim 1, wherein the subject has been diagnosed with cystic fibrosis (CF); asthma; chronic obstructive pulmonary disease (COPD); pulmonary hypertension; lung cancer; pulmonary fibrosis; bronchiectasis; acute respiratory distress syndrome; emphysema; pneumoconiosis; tuberculosis; nontuberculous mycobacterial (NTM) pulmonary infections; SARS; MERS; Covid-19; or pneumonia.

7. The method of claim 1, wherein the biofilm is caused by an antibiotic-resistant strain of a microorganism.

8. The method of claim 7, wherein the microorganism is *S. pneumoniae*, *P. aeruginosa* or *A. fumigatus*.

* * * * *